United States Patent
Maoz et al.

(10) Patent No.: US 12,125,570 B1
(45) Date of Patent: Oct. 22, 2024

(54) SYSTEM AND METHOD FOR CUSTOMER IDENTIFICATION AND WORKFLOW OPTIMIZATION

(71) Applicant: MH SUB I, LLC, El Segundo, CA (US)

(72) Inventors: Or Maoz, Dunwoody, GA (US); Rizwan Zia, Dunwoody, GA (US); Joseph Jackson, Atlanta, GA (US)

(73) Assignee: MH SUB I, LLC, El Segundo, CA (US)

( * ) Notice: Subject to any disclaimer, the term of this patent is extended or adjusted under 35 U.S.C. 154(b) by 633 days.

(21) Appl. No.: 17/336,303

(22) Filed: Jun. 2, 2021

(51) Int. Cl.
*G16H 20/10* (2018.01)
*G06F 16/2457* (2019.01)
*G06Q 10/087* (2023.01)
*H04M 3/493* (2006.01)

(52) U.S. Cl.
CPC ......... *G16H 20/10* (2018.01); *G06F 16/2457* (2019.01); *G06Q 10/087* (2013.01); *H04M 3/493* (2013.01)

(58) Field of Classification Search
CPC .. G16H 20/10; G06F 16/2457; G06Q 10/087; H04M 3/493
See application file for complete search history.

(56) References Cited

U.S. PATENT DOCUMENTS

| | | | | |
|---|---|---|---|---|
| 7,426,476 B2* | 9/2008 | Munoz | ................... | G16H 20/10 |
| | | | | 705/2 |
| 10,811,127 B1* | 10/2020 | Mathur | ............. | H04M 3/42382 |
| 2010/0239075 A1* | 9/2010 | Kobylevsky | ............ | G10L 15/22 |
| | | | | 379/88.01 |
| 2013/0013333 A1* | 1/2013 | Gopinathan | ........... | G06Q 10/10 |
| | | | | 705/2 |
| 2015/0350427 A1* | 12/2015 | Benway | ................ | H04M 3/493 |
| | | | | 379/88.01 |
| 2017/0220741 A1* | 8/2017 | Toupin | ................ | H04M 3/4936 |

\* cited by examiner

*Primary Examiner* — Meredith A Long
(74) *Attorney, Agent, or Firm* — Rutan & Tucker, LLP (57) ABSTRACT

A method id described for controlling operations of a system to support automated communications with a plurality of interactive voice response (IVR) system for fulfillment of a prescription order. The method features a first operation of identifying a destination IVR system based on a request message. Based on content associated with the request message, generating a prescription order to establish a communication session with the destination IVR system. Therefore, one or more data queries are received from the destination IVR system, and responsive to receipt of each data query of the one or more data queries from the destination IVR system, the content associated with the request message is accessed to generate a response to each data query. Thereafter, data associated with each response is translated prior to transmission to the destination IVR system to enable fulfillment of the prescription order.

20 Claims, 6 Drawing Sheets

SYSTEM AND METHOD FOR CUSTOMER IDENTIFICATION AND WORKFLOW OPTIMIZATION

FIELD

Embodiments of the disclosure generally relate to an automated system adapted to interact with multiple types of interactive voice response (IVR) systems to order products and/or services, and in particular, an automated refill order system for a medicinal prescription.

GENERAL BACKGROUND

Currently, to address a malady, a patient obtains a written script for a prescription medication or medication therapy (hereinafter "medicinal prescription") from a physician and physically delivers the medicinal prescription to a pharmacist working at a pharmacy. The pharmacist fills the medicinal prescription and contacts the patient, normally by phone, that the medication is ready for pickup. Thereafter, the patient visits the pharmacy to pick-up the medication and pay any outstanding costs (e.g., co-pay, etc.). Normally, the outstanding costs are the difference between the pharmacy's charge for the medication less any covered benefit under the patient's insurance.

In many cases, a medicinal prescription allows the patient to secure a prescribed number of refills of a medication before the patient needs to be re-evaluated by a physician. Hence, many pharmacies utilize an interactive voice response (IVR) system, which supports pharmacy operations by managing incoming telephone calls requesting a refill of a medicinal prescription, without the patient physically visiting the pharmacy and without the pharmacy hiring additional persons to take medicinal prescription refills over the telephone.

The IVR system is designed to assist pharmacy productivity by reducing the amount of unnecessary interaction time between pharmacists and their patients. This allows pharmacists to avoid unnecessary interruptions for filling medicinal prescriptions, and instead, allows the pharmacy to concentrate on filling medicinal prescriptions, dispensing needed medications, and conducting important discussions with patients about the dispensed medication. The IVR systems are directed primarily to improving efficiencies at the pharmacy, but these systems do not account for saving patients, especially patients of advanced years, time and aggravation in dealing with systems that may be temperamental and prone to error.

BRIEF DESCRIPTION OF THE DRAWINGS

The present invention is illustrated by way of example and not limitation in the accompanying figures, in which like references indicate similar elements, and in which.

DETAILED DESCRIPTION

Embodiments of the present disclosure generally relate to an automated refill order (ARO) system configured to (i) receive request messages from one or more users over a network and, based on content of each request message, (ii) establish a communication session with a selected interactive voice response (IVR) system of a plurality of IVR systems. This communication session may involve the ARO system establishing communications with the selected IVR system, conducting translations of data associated with one or more incoming data queries from the IVR system for processing, and conducting translations of data associated with outgoing responses to each data query. Herein, the plurality of IVR systems may be associated with different targets (companies), and thus, each of these IVR systems may operate in accordance with a different communication scheme such as a different audio-based exchange (e.g., speech-based queries/responses), different keystroke exchanges (e.g., speech-based queries followed by keystroke responses as digital values or audio tones), or any combination thereof. The plurality of IVR systems may be used to coordinate the purchase of a product or service from different medical providers, different retail stores, or the like.

In particular, according to one embodiment of the disclosure, the ARO system may be configured to interact with different pharmacy IVR systems. Based on this embodiment, the ARO system is configured to receive a request message (e.g., electronic email message, web portal access with uploading of prescription-related information delivery, etc.) from a network device utilized by the user (hereinafter, "patient") and parse contents of the request message to retrieve some or all of this content for use in (i) establishing a communication session with an IVR system for a pharmacy identified in the request message and (ii) generating responses to data queries transmitted from the pharmacy IVR system based on content within the request message or metadata accompanying the request message. The parsing of the contents may include accessing different fields of the request message or extracting portions of the prescription-related information from a captured image, printed code (e.g. barcode, QR code, etc.) or the like. Each of the data queries and responses constitute messages generated in accordance with a known communication scheme followed by that pharmacy IVR system.

Herein, the ARO system receives a request message, which constitutes a prescription order, namely a patient's request and consent to refill a medicinal prescription on his or her behalf along with unique prescription-related information pertaining to that patient. According to one embodiment of the disclosure, the request message may include (1) patient's digital consent and (2) prescription-related information including, but not limited or restricted to the following: (a) patient's full name; (b) prescription number; (c) medication name; (d) pharmacy name and/or address; and/or (e) pharmacy's phone number or contact information. The request message may be in the form of an electronic mail (email) message with fillable fields, a web portal access to upload prescription-related information into the ARO system, or the like.

After receipt of the prescription-related information, the ARO system is configured to conduct an initial determination as to whether it is able to process an incoming request message. As an illustrative example, the initial determination may constitute a first analytic operation to determine whether the ARO system is configured to communicate with the IVR system of the pharmacy identified in the request message. The initial determination is conducted by communication control logic deployed within the ARO system. According to one exemplary embodiment, the ARO system features the communication control logic, along with a first translation engine, a second translation engine, monitoring logic, fulfillment timing logic, and a session log. The session log maintains data associated with the operations performed or controlled by the communication control logic, as described below.

More specifically, when configured to process the request message, the communication control logic of the ARO system parses the content of the request message to determine a pharmacy targeted to process the prescription. Thereafter, the ARO system establishes communications with an IVR system of the targeted pharmacy, such as initiates a telephone call to this IVR system. The first and second translation engines are deployed within the ARO system to support communications with different types of IVR systems.

In particular, one embodiment of the ARO system may be configured to include the first translation engine and the second translation engine. The second translation engine conducts a translation of audio associated with a data query provided from the IVR system of the targeted pharmacy. The data query is received by the ARO system in response to a communication session being established with the IVR system. The second translation engine may include a speech-to-text engine to convert one or more audio segments within the data query from the IVR system into digital data for analysis by the communication control logic of the ARO system. The first translation engine may include a text-to-speech engine, which translates portions of the prescription-related information received as part of the request message into one or more audio segments that are responsive to the data query. The audio segments associated with a response emulate human verbal answers to the data queries from the pharmacy IVR system.

Additionally, or in the alternative to the text-to-speech engine, the first translation engine may include keystroke emulation logic, which generates keystrokes (e.g., audible tones or digital values) in response to some or all of the data (audio) queries to emulate depression of certain buttons on a keypad. Communication control logic within the ARO system is configured to control the exchange of the translated data (e.g., digital data from audio queries, audio responses, keystroke tones or values, etc.) with the pharmacy IVR system in efforts to successfully fill or refill a prescription identified within the request message. Hence, the ARO system interacts with the pharmacy IVR system on behalf of the user.

During interaction with the pharmacy IVR system, as described above, the communication control logic within the ARO system is configured to conduct analytics on the digital data produced by the second translation engine from the data queries and generate audio responses to the data queries that are emitted by the ARO system. According to one embodiment of the disclosure, the communication control logic may be configured to conduct a predictive analysis, based on the first data query received from the pharmacy IVR system, as to which type of communication scheme (interactive voice script) is utilized by that pharmacy IVR system. The predictive analysis may be conducted based on a reference model (tree-based series of operations) formulated for the communications conducted by each of the IVR systems or based on a machine-learning model. In particular, the type of communication scheme may identify the predicted type and order of data queries expected from the pharmacy IVR system so that the ARO system operates concurrently to response to data query and formulate subsequent responses anticipated for future data queries.

After message exchanges with the pharmacy IVR system, the ARO system is configured to determine if the medicinal prescription identified in the prescription order was successfully filled or not. If the medicinal prescription will be filled, the communication control logic within the ARO system conducts analytics of a particular audio segment received from the IVR system (e.g., audio from last data query from the IVR system during the communication session) to determine when the prescription medication will be ready for picked up and generates a return message for transmission to the patient (using their preferred communication channel) letting her or him know the prescription order will be filled and estimated pick-up time. Also, the communication control logic communicates with the monitoring logic to identify that the request message was successfully completed.

However, if the medicinal prescription cannot be filled, the ARO system is configured to determine the reason for the failure based on feedback messages received from the IVR system. The feedback messages may constitute audio received from the IVR system and/or messages transmitted from the IVR system over a different transmission medium. Additionally, or in the alternative, the ARO system may be configured to determine the reason for the failure based on an analysis of the content of the session log, which includes information associated with the operations conducted by the ARO system in handling each request message and the order of occurrence of these operations.

If the medicinal prescription cannot be filled based on a technical issue between the ARO system and the pharmacy IVR system, the request message will be re-routed to a datacenter (e.g., one or more human agents). Upon receipt of the request message, a human agent is tasked to converse with the pharmacy IVR system to request the medicinal prescription to be filled, and if successful, upload at least some of the prescription-related information (e.g., prescription number) and the estimated pick-up time learned from the agent to the ARO system for generation of the return message. If the medicinal prescription could not be filled due to a non-technical issue (e.g., prescription refill is too early, medication is out of stock, etc.), the ARO system is configured to generate a return message to the patient, letting her or him know that the prescription order failed and the reason for the failure. The pharmacy contact information may be included in the return message, allowing the patient to contact the pharmacy directly. For both of these scenarios, however, the communication control logic communicates with the monitoring logic to identify that the request message was not successfully completed.

Upon determining that a prescribed threshold associated with a particular IVR system has been reached in connection with failed request messages (e.g., failure/success ratio exceeds a prescribed threshold, success/failure ratio falls below a prescribed threshold, number of failures or successive failures exceeds a prescribed threshold, etc.), the monitoring logic notifies an administrator of a potential operational issue with the ARO system. For example, the potential operational issue may be caused by a potential change in the communication scheme followed by the particular IVR system. If so, the communication control logic may need to be updated and/or artificial intelligence (AI) engine, operating at least in part as the communication control logic, may need to be further trained.

Also, during operations in handling each request message, the fulfillment timing logic monitors each request message to determine that the request message is completed within a prescribed time period. If not, upon determining that the request message has failed to be handled by the ARO system within a first prescribed time period, the fulfillment timing logic may prompt the content of the request message to be passed to the datacenter for an agent to handle the prescription order with the pharmacy IVR system. Upon determining that the request message has failed to be handled by the datacenter within a second prescribed time period, the fulfillment timing logic may conclude that the prescription order cannot be fulfilled and cause the ARO system to issue a return message regarding the same, as described above.

I. Terminology

In the following description, certain terminology is used to describe aspects of the invention. In certain situations, the terms "logic" and "engine" are representative of hardware, firmware, and/or software that is configured to perform one or more functions. As hardware, the logic (or engine) may include circuitry having data processing and/or storage functionality. Examples of such circuitry may include, but are not limited or restricted to a processor, a programmable gate array, a microcontroller, an application specific integrated circuit, wireless receiver, transmitter and/or transceiver, semiconductor memory, or combinatorial logic.

Alternatively, or in combination with the hardware circuitry described above, the logic (or engine) may be software in the form of one or more software modules, which may be configured to operate in the same manner as its counterpart circuitry. For instance, a software module may be a software instance that operates as a processor, namely a virtual processor whose underlying operations is based on a physical processor such as an EC2 instance within the Amazon® AWS infrastructure for example. Additionally, a software module may include an executable application, a daemon application, an application programming interface (API), a subroutine, a function, a procedure, an applet, a servlet, a routine, source code, a shared library/dynamic load library, or even one or more instructions.

The software module(s) may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; a semiconductor memory; non-persistent storage such as volatile memory (e.g., any type of random access memory "RAM"); persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic (or module or engine) may be stored in persistent storage.

The term "computerized" generally represents that any corresponding operations are conducted by hardware in combination with software and/or firmware.

The term "network device" should be generally construed as a physical or virtualized device with data processing capability and/or a capability of connecting to a network, such as a public cloud network (e.g., Amazon Web Service (AWS®), Microsoft Azure®, Google Cloud®, etc.), a private cloud network, a public network (e.g., Internet), or any other network type. Examples of a network device as a physical device may include, but are not limited or restricted to, the following: a server, a router or other intermediary communication device, an endpoint (e.g., a laptop, a smartphone, a tablet, a desktop computer, a netbook, etc.), or the like. As a virtualized device, the network device is software with similar functionality as the physical device. The network device may also be deployed as part any physical or virtualized device communicatively coupled via a device interface (e.g., API(s)) for gaining access to the automated refill order (ARO) system as described below.

The term "order" corresponds to a type of message (prescribed, structured data format) that is intended to result in a particular task to be performed. The task may include commencement of a series of data queries that are organized to solicit information needed by a pharmacist to fill a medicinal prescription for example. The term "message" generally refers to information placed in a prescribed format and transmitted in accordance with a suitable delivery protocol or information provided to (or made available from) a logical data structure such as a prescribed API in order to perform a prescribed operation. Examples of a delivery protocol may include, but are not limited or restricted to User Datagram Protocol (UDP), Transmission Control Protocol (TCP); or the like. Hence, each message may be in the form of one or more packets, frame, instruction such as a command, or any other series of bits having the prescribed, structured format.

The term "transmission medium" generally refers to a medium that supports communications between a source and a destination. For instance, to support audio communications, the transmission medium may include wired interconnects in the form of Plain Old Telephone Services (POTS) telephone lines, electrical wiring, optical fiber, cable, or the like. Additionally, or in the alternative, the transmission medium may include components that support wireless communications such as wireless receiver(s), wireless transmitter(s) and/or wireless transceiver(s) situated at a source and/or a destination.

Finally, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As this invention is susceptible to embodiments of many different forms, it is intended that the present disclosure is to be considered as an example of the principles of the invention and not intended to limit the invention to the specific embodiments shown and described.

II. System Architecture

Figure 1:
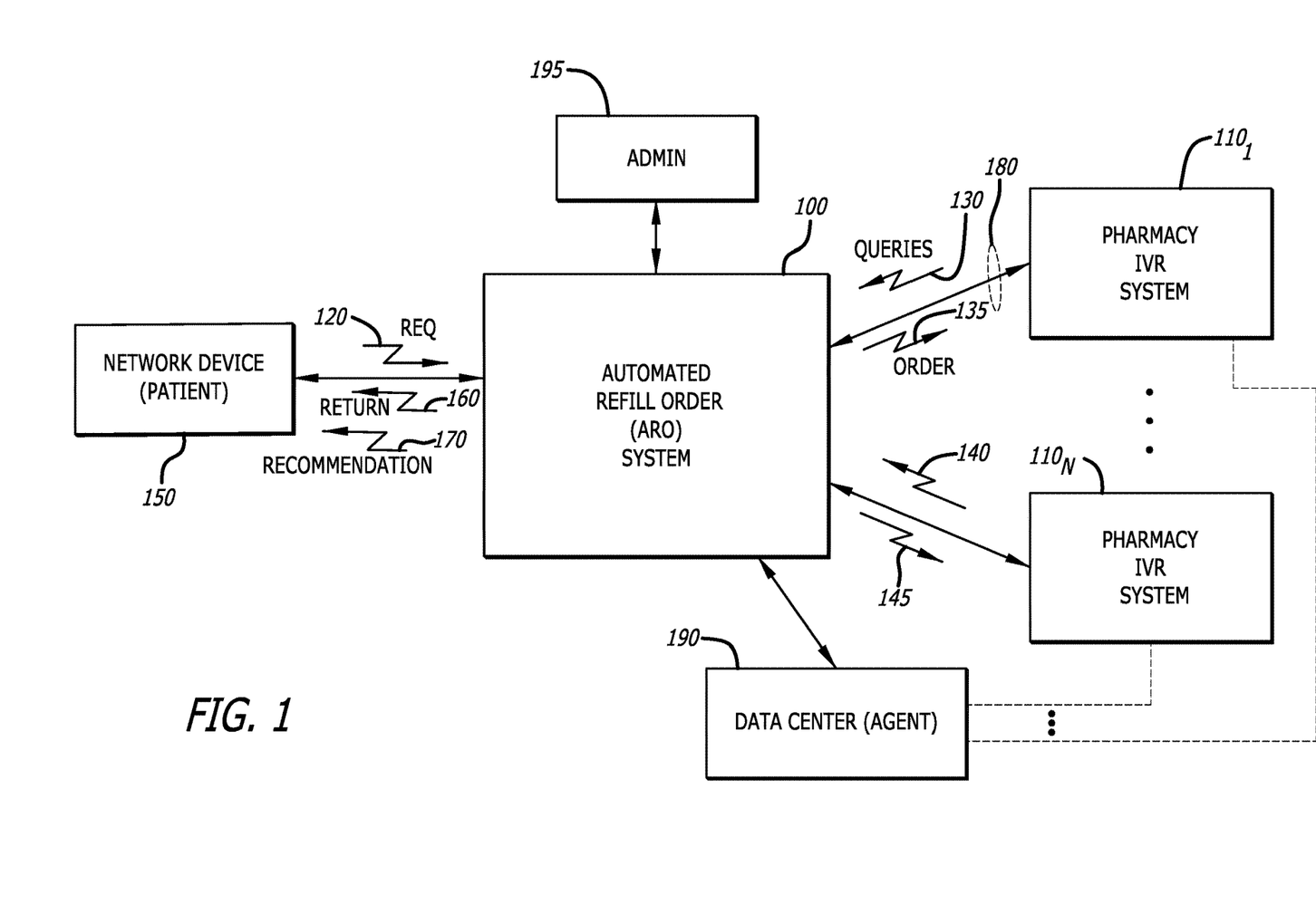
FIG. 1 illustrates an exemplary embodiment of automated refill order (ARO) system operating to interact and initiate a prescription order to a pharmacy interactive voice response (IVR) system in response to a request message.

Referring to FIG. 1, an exemplary embodiment of automated refill order (ARO) system 100 operating to fulfill a request (REQ) message 120 directed to one of a plurality of (targeted) systems $110_1$-$110_N$ (N>1), such as system $110_1$ for example, is shown. Each of these systems $110_1$-$110_N$ may correspond to an IVR system associated with a different enterprise (e.g., company, partnership, co-op, etc.), and each of the IVR systems $110_1$-$110_N$ may operate in accordance with a different communication scheme. For example, according to one embodiment of this disclosure, a first IVR system $110_1$ may be associated with a first pharmacy chain (e.g., WALMART® pharmacy), which operates in accordance with a first communication scheme by initiating a first series of data queries 130 to the ARO system 100. The first series of data queries 130 are in response to receiving a prescription order 135 submitted by the ARO system 100. Similarly, a $N^{th}$ IVR system $110_N$ may be associated with a second pharmacy chain (e.g., RITEAID® pharmacy), which operates in accordance with a second communication scheme by initiating a second series of data queries 140 to the ARO system 100 in response to a prescription order 145.

As described above, the first series of data queries 130 is a different communication scheme than the second series of data queries 140. This difference may be due to a number of factors, such as a different data query order, different types of queries, or different response type such as audio segment or keystroke tone/value. Exemplary data queries conducted by different IVR systems are shown below and the ARO system 100 may be configured to process the data queries received from an IVR system in accordance with a predicted communication scheme (series) based on the type of first data query in the series of data queries:

| [First series of data queries] | [Second series of data queries] |
| --- | --- |
| Q1: Request patient's name to be stated | Q1: Request prescription number using keypad |
| Q2: Request doctor's name to be stated | Q2: Request patient's name to be stated |
| Q3: Request prescription number to be stated | Q3: Request desired pick-up time using keypad |

Figure 2:
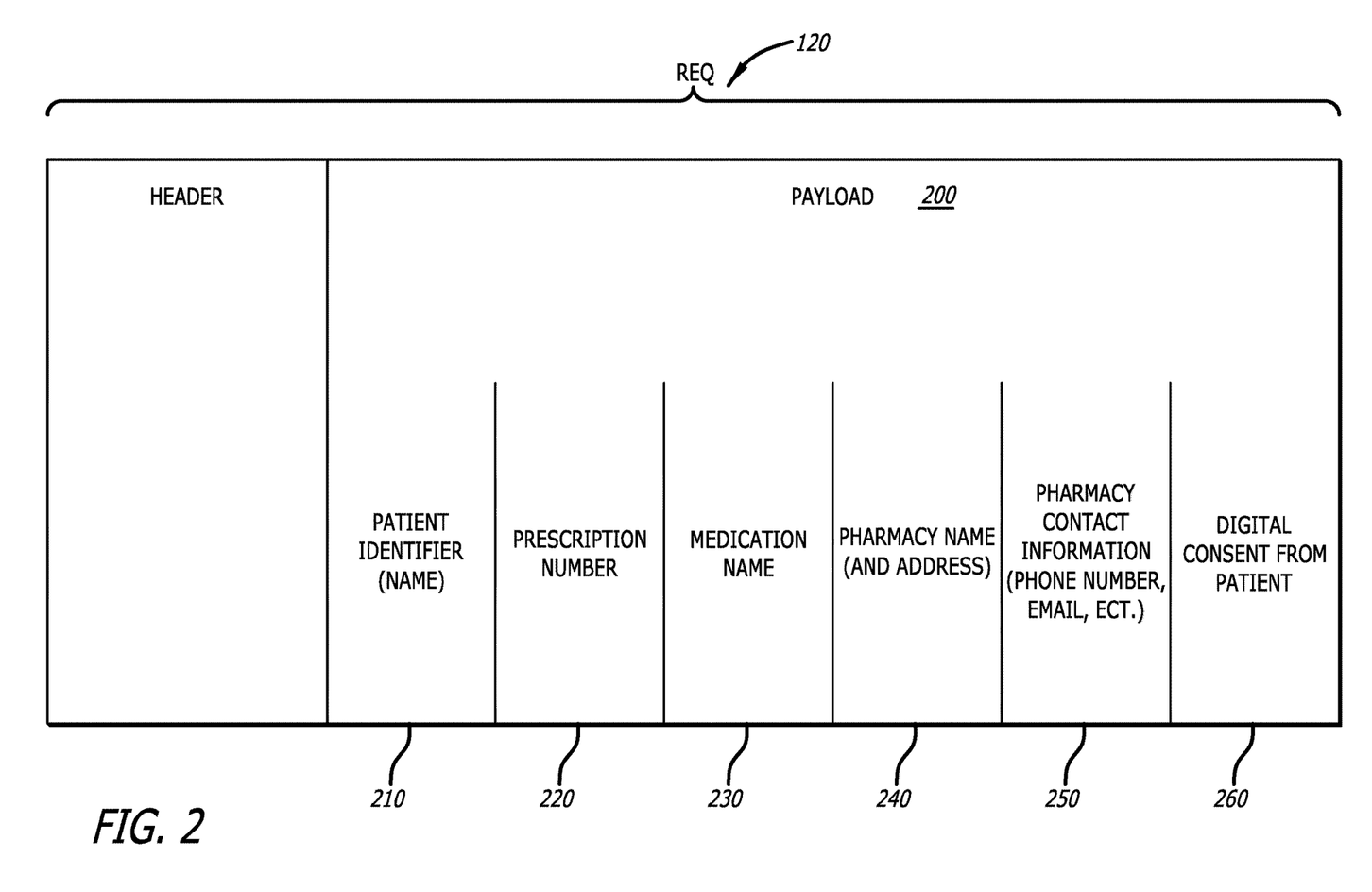
FIG. 2 illustrates an exemplary embodiment of a data structure for the request message initiated by a network device managed by a user as shown in FIG. 1.

More specifically, the ARO system 100 is configured to receive, as input, the REQ message 120 from a network device 150. As shown in FIG. 2, the REQ message 120 may constitute an electronic email message featuring a header and a payload 200 featuring prescription-related information. Alternatively, the REQ message 120 may constitute the patient-related information uploaded via an access to a web portal supported by the ARO system 100 via a graphical user interface (GUI) provided by the ARO system 100.

The prescription-related information may include, but is not limited or restricted to the following: (1) patient's full name 210; (2) prescription number 220; (3) medication name 230; (4) pharmacy name and/or address 240; and/or (5) pharmacy contact information such as the phone number 250. The patient's digital consent 260 may be provided. The content associated with the sixth data field, namely the patient's digital consent 260, may be utilized by the ARO system 100 to conduct a first determination as to whether the user (patient) has provided permission to the ARO system 100 to proceed with fulfillment of a medicinal prescription on her or his behalf. Such permissions may be compliant with the Health Insurance Portability and Accountability Act (HIPPA).

Referring back to FIG. 1, if no digital consent is provided with the REQ message 120 (or no digital consent is maintained by the ARO system 100 based on a prior request for a medicinal prescription refill), the ARO system 100 may be configured to generate a return message 160 requesting the user to include the digital consent 260 with a secondary REQ message to enable the ARO system 100 to fill the prescription. Also, the ARO system 100 may be configured to remove the REQ message 120 from a data store/queue utilized for retaining content prior to processing by the ARO system 100.

However, upon receipt of the digital consent 260 (or location of the stored digital consent 260), the ARO system 100 may be configured to conduct analytics on the prescription-related information. For instance, according to one embodiment of the disclosure, the analytics may include parsing the prescription-related information to recover the patient's pharmacy name and/or address 240 to determine whether the ARO system 100 is configured to generate a prescription order (e.g., first prescription order) 135 for submission to the identified pharmacy (e.g., WALMART® pharmacy). According to another embodiment of the disclosure, the analytics may include recovering prescription-related information from an image (e.g., barcode, QR code, picture of label, etc.) and automatically parsing the same to recover the patient's pharmacy name and/or address 240.

Where the identified pharmacy is not supported, the ARO system 100 may notify the user by generating a recommendation message 170, which identifies a different pharmacy supported by the ARO system and awaits a message (not shown) from the user permitting transmission of the prescription order 135 to the different pharmacy. Herein, the selection of the different pharmacy may be based on the geographic location of the network device 130 (e.g., cellular telephone). The geographic location may be obtained from the IP address of the network device 150, nearest cellular tower that forwarded the REQ message 120 to the ARO system 100, or geographic information provided by the network device 150 as information included as part of (or accompanying) the REQ message 120. Alternatively, the different pharmacy may be selected based on known pricing for certain medications supplied by different pharmacies and automated selection of the pharmacy providing the most cost-effective medication. The costs may be uploaded into the ARO system 100 by pharmacies or pharmacy chains, where the upload periodicity may be hourly, daily, weekly, or the like.

Herein, the prescription order 135 may constitute a message directed to the IVR system $110_1$ to commence an exchange of data to fill the prescription order 135. The prescription order 135 may be configured to merely establish communications over a transmission medium 180 between the ARO system 100 and the IVR system $110_1$. Thereafter, the ARO system 100 relies on the content of the REQ message 120 to generate appropriate responses to the series of data queries 130 initiated by the IVR system $110_1$. The responses may be generated in real-time or may be generated in advance where the series of data queries is known in advance or the next data query may be predicted based on known series of data queries that commence with a first data query provided from the IVR system $110_1$.

Figure 3:
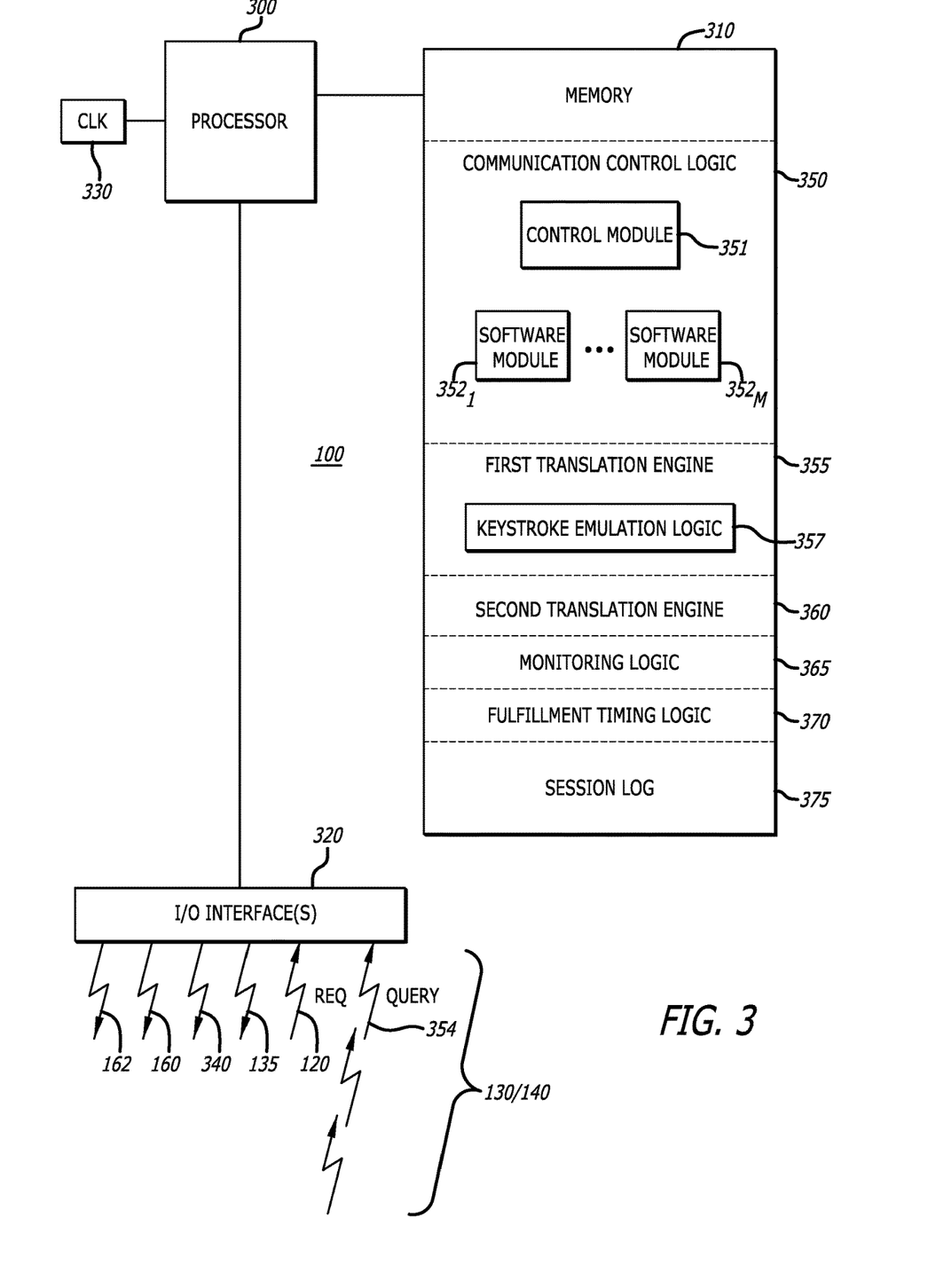
FIG. 3 illustrates a first exemplary embodiment of the ARO system of FIG. 1.

Referring now to FIG. 3, a first exemplary embodiment of the ARO system 100 of FIG. 1 is shown. Herein, the ARO system 100 includes a processor 300, a memory 310, one or more input/output (I/O) interfaces 320 and a clock element 330. The clock element 330 is configured to provide timing for fulfillment timing logic 370 to monitor an amount of time that a prescription order is outstanding prior to being filled by the pharmacist. If the amount of time exceeds a first threshold, the automated process for fulfillment of the prescription order 135 is determined to have failed, and the content of the REQ message 120 is provided to a datacenter 190 of FIG. 1 for handling manually. If the amount of time exceeds a second threshold, however, the datacenter 190 has failed to fill the prescription order 135 within a prescribed time period, and as a result, the communication control logic 350 generates a "timeout" message 340 to notify the user that fulfillment of the prescription order was unsuccessful. The timeout message may include the reasons for the ARO system's inability to fill the prescription order 135 along with (i) prescription number 220, (ii) medication name 230, (iii) pharmacy name and/or address 240, and/or (iv) pharmacy phone number 250 that were included as part of the REQ message 120.

According to one exemplary embodiment, as shown in FIG. 3, the ARO system 100 includes the processor 300, which is configured to execute software components maintained within the memory 310. The software components may include, but are not limited or restricted to the communication control logic 350, a first translation engine 355, a second translation engine 360, monitoring logic 365 and the fulfillment timing logic 370. The memory 310 may include a data store, identified as a session log 375. The session log 375 maintains data associated with the operations performed by the communication control logic 350 that, in response to a technical failure in communications between the ARO system 100 and the IVR system $110_1$, a determination can be made (by the ARO system 100 or an administrator 195) as to the reasons surrounding the technical failure (i.e., where in the communication scheme did the failure occur).

Communicatively coupled to one or more I/O interfaces 320, the communication control logic 350 is configured to collect content from the REQ message 120, received via the I/O interface(s), for use by the first translation engine 355 in handling the data queries. Additionally, the communication control logic 350 may be configured to control operability of the ARO system 100, including interaction with other logic and engines. For this embodiment, the communication control logic 350 may feature a control module 351 and one or more software modules $352_1$-$352_M$ (M≥1), where each software module $352_1$-$352_M$ is configured to interact with a particular IVR system or a particular set (two or more) of IVR systems as determined by the control module 351. For example, based on the content of the REQ message 120, the control module 351 may be configured to establish communications with the IVR system $110_1$ and, depending on content of a first data query 354 initiated by the IVR system $110_1$, operate in accordance with particular communication scheme supported by a first software module $352_1$. The first data query 354 is part of a series of data queries such as the first or second series of data queries 130/140 as shown in FIG. 1.

Stated differently, based on determining that the first data query 354 constitutes a first query type, the control module 351 predicts the communication scheme (e.g., the first series data queries 130 based on a review of known sequences of queries stored in a data store or reference model generated for each the IVR systems) utilized by the IVR system $110_1$ and activates at least one of the software modules $352_1$-$352_M$ (e.g., first software module $352_1$) to conduct operations directed toward generating responses to the first series data queries 130. Alternatively, where the first data query 354 corresponds to a second query type different than the first query type, the control module 351 may be configured to predict a communication scheme (e.g., the second series data queries 140) utilized by the IVR system $110_2$ and activates one or more of the software modules $352_1$-$352_M$ (e.g., first software module $352_2$) to conduct operations directed toward generating responses to the second series data queries 140.

As further shown in FIG. 3, according to one embodiment of the disclosure, the first translation engine 355 may include a text-to-speech engine, which translates certain alphanumeric text provided within the REQ message 120 into an audio segment. The audio segment is audio of a short duration (e.g., less than a few seconds) that emulates an initial verbal query and verbal responses to data queries provided by an IVR system (e.g., IVR system $110_1$). Additionally, or in the alternative to the text-to-speech engine, the first translation engine 355 may include keystroke emulation logic 357, which translates alphanumeric text provided within the REQ message 120 into keystrokes (e.g., audible tones or digital values). The keystroke emulation logic 357 emulates selection (e.g., depression) of certain keys on a telephone or cellular telephone keypad. The first translation engine 355 operates concurrently with the communication control logic 350 in efforts to successfully fill or refill a medication identified within the REQ message 120.

The second translation engine 360 may include an audio-to-text engine, which translates audio associated with a data query (e.g., first data query 354), received from any of the IVR systems $110_1$-$110_N$ (e.g., IVR system $110_1$) of FIG. 1, into alphanumeric text. The alphanumeric text corresponds to digital data, which is analyzed by the communication control logic 350 to determine what data, if any, is needed to respond to the data query. The data is supplied as part of the REQ message 120 and the operations conducted by the communication control logic 350 in responding to data queries are recorded in the session log 375.

More specifically, during interaction with the IVR system $110_1$ for the identified pharmacy, as described above, the communication control logic 350 is configured to conduct analytics on the content of the data queries received from the second translation engine 360 and generate responses that are converted into audio responses by the first translation engine 355 for transmission to the IVR system $110_1$. The analytics may include a determination of the subject matter of the data queries for generating responses based on content associated with the REQ message 120. The analytics may further include a determination of a type of data query, especially for the first data query 354, for predicting the type/order of further data queries based on known communication schemes observed by the IVR systems $110_1$-$110_N$ for improved system efficiency.

Thereafter, after successful completion of the set of data queries 130/140 from the IVR system $110_1$, the communication control logic 350 is configured to determine if the prescription order was successfully filled or not. When the prescription order was successfully filled, the communication control logic 350 conducts analytics of an audio segment received from the IVR system $110_1$ toward the end of the communication session to (i) determine when the medicinal prescription is ready for picked up and (ii) generate the return message 160. The return message 160 may be transmitted to the user using his or her preferred communication channel (e.g., email, text, audio call, etc.) and advising the user that the prescription order was submitted and the estimated pick-up time. Also, the communication control logic 350 communicates with the monitoring logic 365 to identify that the prescription order 135 associated with the REQ message 120 was successfully completed.

However, when the prescription order 135 has failed to be completed, the communication control logic 350 conducts analytics of the content of the session log 375 to determine the reason or reasons for the failed prescription order. The reason(s) for the failed prescription order may be ascertained by parsing content of the session log 375, which includes information associated with the operations conducted by the ARO system 100 in generating and transmitting responses 130 to the data queries associated with each REQ message.

Where the failed prescription order is based on a technical issue between the ARO system 110 and the IVR system $110_1$, the communication control logic 350 forwards content included in the REQ message 120 to the datacenter (human agent) for manual fulfillment. However, if the failed prescription order is based on a non-technical issue (e.g., prescription refill is too early, medication is out of stock, etc.), the communication control logic 350 is configured to generate the failed order message 162 to the source network device 150, letting the user know that the prescription order failed and the reason(s) for the failure. The pharmacy contact information is included in the return message 160 to enable the patient to more easily contact her or her pharmacy. Also, the communication control logic 350 communicates with the monitoring logic 365 to identify that the REQ message 120 was not successfully completed.

The monitoring logic 365 is configured to monitor the success and/or failure rate in fulfillment of the prescription. Upon determining that a first prescribed threshold has been reached in connection with failed prescription orders (e.g., failure/success ratio exceeds the first prescribed threshold, success/failure ratio falls below the first prescribed threshold, number of successive failures exceeds the first prescribed threshold, etc.), the monitoring logic 365 notifies an administrator of a potential operational issue with the ARO system 100, which may be caused by a potential change of operation in the IVR system $110_1$. If so, the communication control logic 350 (or data accessed thereby) may need to be updated.

Also, during operations in handling the REQ message 120, the fulfillment timing logic 370 monitors each REQ message 120 to determine that the REQ message 120 is processed and the prescription order is filled within a first time period. If not, the fulfillment timing logic 370 detects that the REQ message 120 has not been timely processed, which may prompt the content of the REQ message 120 to be passed to the datacenter 190 for an agent to handle the prescription order with the IVR system $110_1$. Similarly, where the fulfillment timing logic 370 determines that the manual fulfillment was not completed within a second period of time, which is longer in duration than the first period of time, the fulfillment timing logic 370 identifies the REQ message 120 has "failed," which may prompt the communication control logic 350 to generate the failed order message 162 to the source network device 150, advising the patient that the prescription order 135 failed and the reason for the failure as gathered from the session log 375.

Figure 4:
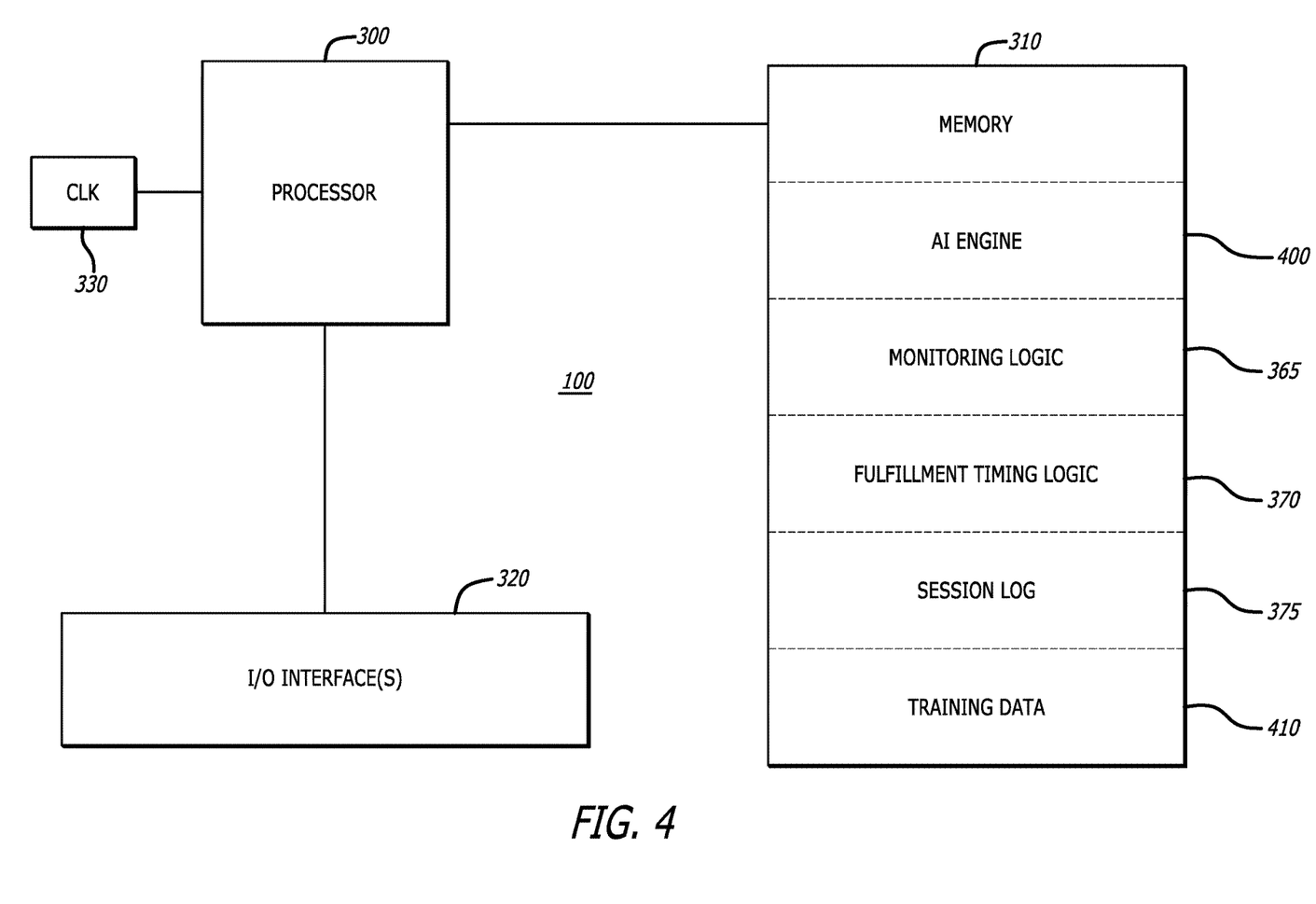
FIG. 4 illustrates a second exemplary embodiment of the ARO system of FIG. 1.

Referring now to FIG. 4, a second exemplary embodiment of the ARO system 100 of FIG. 1 is shown. As in FIG. 3, the ARO system 100 includes the processor 300, the memory 310, the I/O interface(s) 320 and the clock element 330. However, the processor 300 of the ARO system 100 is configured to execute different types of software components maintained within the memory 310. In particular, the software components may include, but are not limited or restricted to an artificial intelligence (AI) engine 400, which operates in concert with the monitoring logic 365 and the fulfillment timing logic 370. As below, the memory 320 may further include the session log 375, which maintains data associated with the operations performed by the AI engine 400 so that, in response to a failed prescription order, the AI engine 400 can conduct analytics to determine the reasons surrounding the failure (i.e., technical or non-technical, specific operation(s) that caused the failed prescription order, etc.). The AI engine 400 is trained to interact with different IVR system types.

As shown in FIG. 4, when executed by the processor 300, the AI engine 400 is configured to collect content from the REQ message 120 received via the I/O interface(s) 320 and perform analytics on content of the REQ message 120. Such analytics are conducted to establish a communication session with an IVR system identified in the REQ message 120 (e.g., IVR system $110_1$) and to generate responses to data queries initiated by the IVR system $110_1$. For example, based on the content of the REQ message 120, the AI engine 400 may be configured to establish communications with the IVR system $110_1$ and is trained to generate responses to a series of data queries conducted by the IVR system $110_1$. Such training may be conducted periodic through the use of training data 410 (e.g., prescription orders that are known to be successfully filed and/or failed) associated with each IVR system supported by the ARO system 100. The AI engine 400 may be configured with response generation analytic logic that determines a response to a first data query from an IVR system $110_i$ ($1 \le i \le N$) in real time, and based on the response (or type of data query), predicts a data query sequence provided from the IVR system $110_i$. The AI engine 400 is configured to support a plurality of different types of data query sequences in which the content for each data query is evaluated and continues along the chosen data query sequence or adjusts to continue along another data query sequence. Herein, the AI engine 400 is trained to automate the operability of the communication control logic 350, the first translation engine 355 and the second translation engine 360 of FIG. 3, while the monitoring logic 365 and the fulfillment timing logic 370 operate in the same manner as described above.

III. System Operability

Figure 5A:
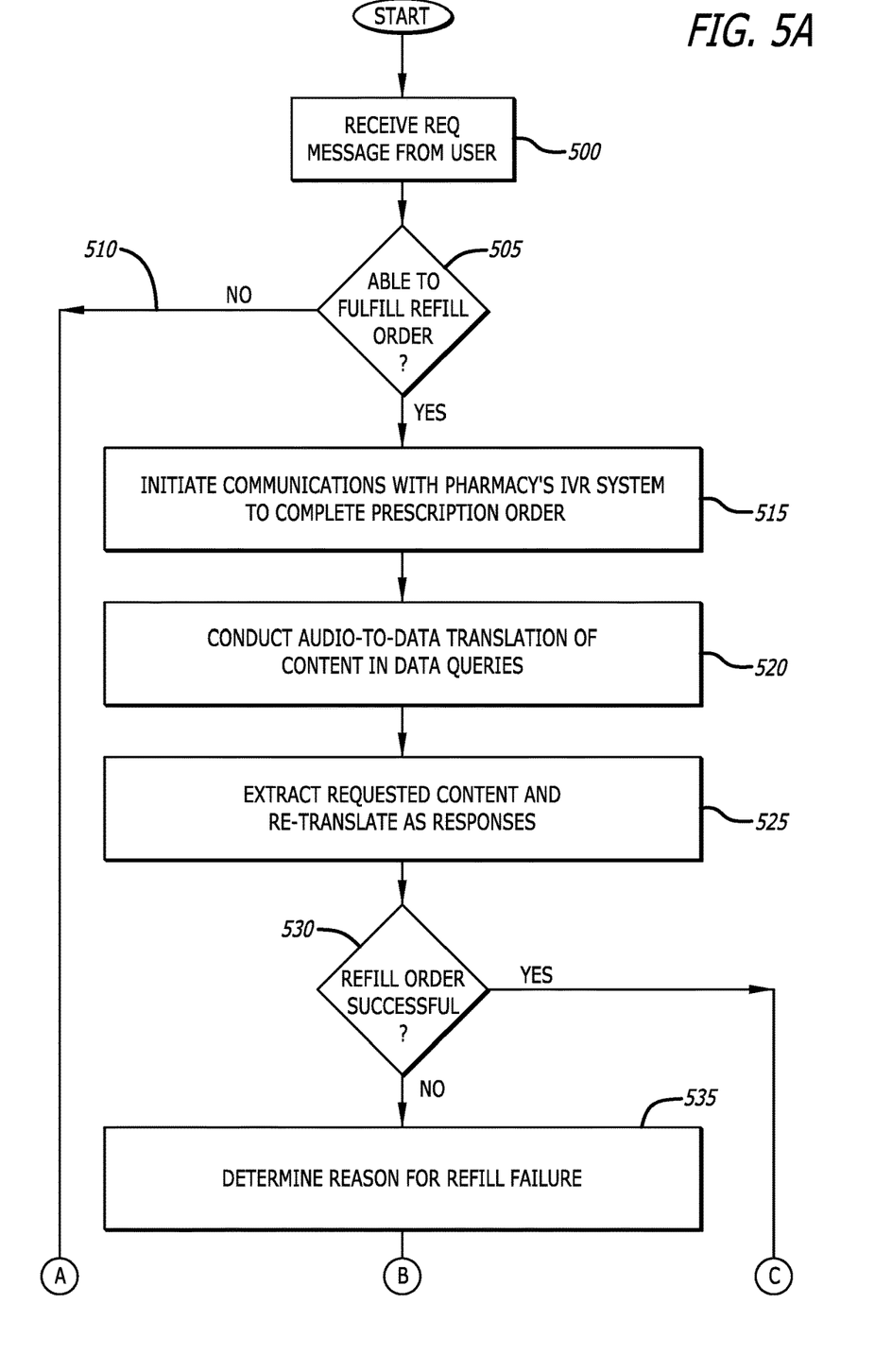
FIGS. 5A-5B illustrate an exemplary embodiment of operations conducted by the ARO system in handling a request message such as a prescription order.
Figure 5B:
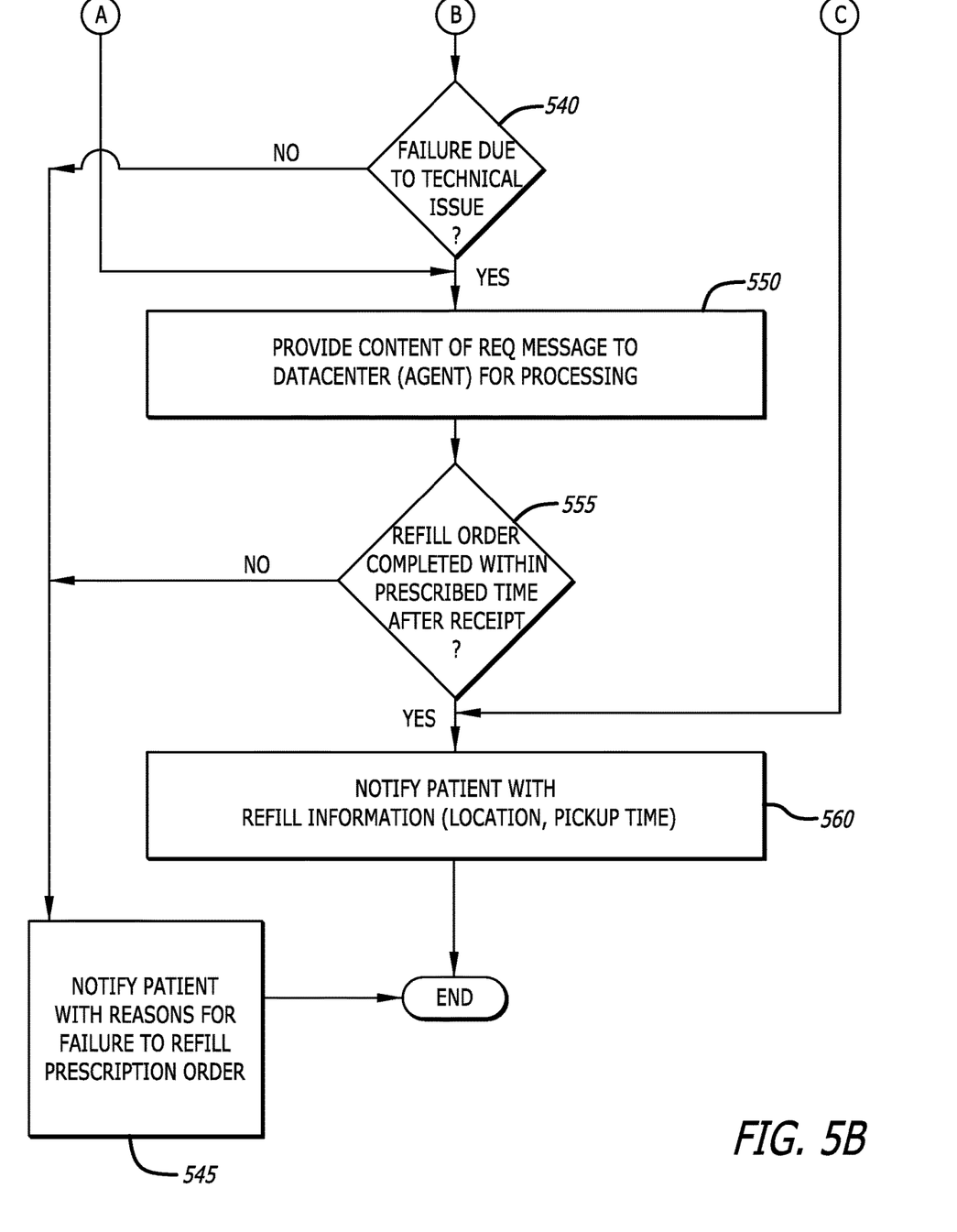

Referring now to FIGS. 5A-5B, an exemplary embodiment of operations conducted by the ARO system 100 of FIG. 1, FIG. 3 and/or FIG. 4 in handling automated fulfillment of a prescription order by any of a plurality of IVR systems in response to a request (REQ) message is shown. Upon receipt of the REQ message from a patient, the ARO system determines whether it is configured (and able) to fulfill a prescription order (blocks 500 and 505). The prescription order may be directed to refilling a medicinal prescription. If the ARO system is not configured to fulfill the prescription order, in the event that the unable to fulfill the prescription order is not due to the selected pharmacy not be supported by the ARO system (corrected through the recommendation message(s) described above), the ARO system provides the contents of the REQ message to a datacenter (agent) for manual processing of the prescription order (block 510). Otherwise, the ARO system initiates communications with the IVR system identified in the REQ message to complete the prescription order (block 515).

After communications with the IRV system is established, the ARO system conducts translations of audio included in data queries from the IRV system into data that is processed to determine the content requested by the audio (block 520). The requested content is extracted from information provided as part of or with (meta-information) the REQ message and subsequently translated into a format (e.g., audio segment, keystrokes, etc.) expected by the IRV system (block 525). After conclusion of a series of data query/response exchanges, the ARO system determines whether the prescription order was accepted to be filled by the pharmacy associated with the IRV system (block 530). If the prescription order is to be filled, the ARO system receives the pick-up time in which the medicinal prescription is available for pickup and the pick-up details (e.g., pharmacy address, pick-up time, prescription number, etc.) is provided to the patient (block 560). Otherwise, the fulfillment of the prescription order is handled manually or the patient is notified of the inability for the ARO system to complete the prescription order.

In particular, if the prescription order could not be filled, the ARO system is configured to determine the reason for the prescription order being unable to be filled (block 535). This may be achieved by logic within the ARO system reviewing content of a session log, namely data associated with the communication session. The ARO system determines if the failure was due to a technical error or a non-technical error (block 540). If the failure was due to a non-technical error (e.g., medication is unavailable, prescribed number of refills exceeded, prescription refill is too soon, etc.), the patient is notified that the prescription order could not be fulfilled through the ARO system along with a description of the non-technical error (block 545).

However, if the failure was due to a technical error (e.g., communication exchange between the ARO system and the IVR system failed), the content of the REQ message is provided to the datacenter to manually process the prescription order (block 550). This may involve a human agent contacting the IVR system directly to fulfill the prescription. The human agent may be provided information from the session log to understand as to where the error occurred and allow the agent to generate a report to a network administrator to confirm that an update of the operability of the communication control logic or AI engine is necessary for communications with the IVR system. During this process, the ARO system determines that the prescription order is being completed within a prescribed period of time after receipt by the ARO system (block 555). If the datacenter is unable to complete the prescription order or the prescribed period of time has elapsed prior to fulfilling the prescription order, the patient is notified that the prescription order could not be fulfilled through the ARO system along with a description of the non-technical error (block 545). Otherwise, the data center provides the pickup time to the ARO system, which generates a message to the patient to notify her or him of the pick-up time in which the medicinal prescription is available and the pick-up details such as pharmacy address, pick-up time, prescription number, or the like (block 560).

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention.

What is claimed is:

1. A method for controlling operations of a system to support automated communications with a plurality of interactive voice response (IVR) system for fulfillment of a prescription order, the method comprising:
   identifying a destination IVR system based on a request message;
   based on content associated with the request message, generating a prescription order to establish a communication session with the destination IVR system;
   receiving one or more data queries from the destination IVR system;
   responsive to receipt of each data query of the one or more data queries from the destination IVR system, accessing the content associated with the request message to generate a response to each data query by at least translating, by a first translation engine, one or more audio segments associated with a query of the one or more queries into first digital data; and
   translating data associated with each response prior to transmission to the destination IVR system into at least one audio segment to enable fulfillment of the prescription order.

2. The method of claim 1, wherein the content associated with the request message includes a prescription medication name, a prescription number, a pharmacy name and contact information.

3. The method of claim 1, wherein the accessing of the content associated with the request message to generate the response further includes conducting an analytic operation on a first data query of the one or more queries to predict a sequenced order of data queries following the first data query.

4. The method of claim 1, wherein identifying of the destination IVR system from the plurality of IVR systems is based on content of a request message.

5. The method of claim 1, wherein the identifying of the destination IVR system further comprises determining whether the destination IVR system associated with a first pharmacy provides a lowest cost for a medication identified in the request message based on known pricing for the medication, and if not, selecting an IVR system associated with a second pharmacy providing the lowest cost for the medication as the destination IVR system.

6. The method of claim 1 further comprising:
   responsive to fulfillment of the prescription order cannot be achieved based on a technical issue between the system and the destination IVR system, routing the request message to a datacenter for handling by a human agent to attempt to fulfill the prescription order.

7. The method of claim 1 further comprising:
   responsive to fulfillment of the prescription order cannot be achieved based on a non-technical issue between the system and the destination IVR system, generating a return message to a source of the request message, the return message including pharmacy contact information.

8. The method of claim 7, wherein the non-technical issue includes a condition in which the prescription order is being attempted earlier than permitted or a medicine associated with the prescription order is out of stock.

9. An automated refill system, comprising:
   one or more processors; and
   a non-transitory storage medium communicatively coupled to the one or more processors, the non-transitory storage medium comprises a first translation engine that, when executed by the one or more processors, translates one or more audio segments associated a data query of a plurality of data queries from an interactive voice response (IVR) system into first digital data;
   a second translation engine that, when executed by the one or more processors, translates second digital data responsive to the data query into audio for transmission to the IVR system; and
   a communication control logic configured to, when executed by the one or more processors, to (i) process a request message by at least conducting an initial determination whether the automated refill system is configured to communicate with the IVR system identified in the request message, (ii) generating a prescription order to the IVR system that prompts the IVR system to initiate a plurality of data queries including the data query, and (ii) process the first digital data to collect the second digital data based on content associated with the request message and responsive to the data query, wherein the non-transitory storage medium further comprises logic configured to determine whether the IVR system associated with a first pharmacy provides a medication identified in the request message at a lowest cost based on known pricing for the medication, and if not, selecting an IVR system associated with a second pharmacy providing the lowest cost for the medication as the IVR system to which the automated refill system communicates.

10. The automated refill system of claim 9, wherein the communication control logic conducts the initial determination as to whether the automated refill system is configured to communicate with the IVR system identified in the request message by at least conducting a predictive analysis, based on a first data query of the plurality of data queries, as to which type of interactive voice script is being utilized and associating the determined interactive voice script to the IVR system.

11. The automated refill system of claim 9, wherein the communication control logic is further configured to predict a sequenced order of the plurality of data queries utilized by the IVR system based on the first data query, and activates at least one software module to conduct operations directed toward generating responses to the plurality of data queries.

12. The automated refill system of claim 9, wherein the prescription order includes a prescription medication name, a prescription number, a pharmacy name and contact information.

13. The automated refill system of claim 9, wherein the non-transitory storage medium further comprises monitoring logic configured to monitor a success rate or a failure rate in fulfillment of the prescription order and notifying an administrator of a potential operational issue with the automated refill system if the success rate falls below a first prescribed threshold or the failure rate exceeds a second prescribed threshold different than the first prescribed threshold.

14. The automated refill system of claim 13, wherein responsive to if the success rate falling below the first prescribed threshold or the failure rate exceeding the second prescribed threshold, the monitoring logic notifies an administrator of a potential operational issue with the automated refill system.

15. The automated refill system of claim 9, wherein the non-transitory storage medium further comprises fulfillment timing logic to monitor an amount of time that the prescription order is outstanding prior to being filled, the prescription order being provided to a datacenter for handling when a first period of time after receipt of the prescription order has elapsed.

16. The automated refill system of claim 15, wherein the fulfillment logic determines that the prescription order cannot be filled based on a technical issue directed to communications with the IVR system, routing the request message to a datacenter for handling by a human agent to attempt to fulfill the prescription order.

17. The automated refill system of claim 15, wherein the fulfillment logic determines that the prescription order cannot be filled based on a non-technical issue involving communications with the IVR system, generating a return message to a source of the request message, the return message including pharmacy contact information.

18. The automated refill system of claim 17, wherein the non-technical issue includes a condition in which the prescription order is being attempted earlier than permitted or a medicine associated with the prescription order is out of stock.

19. The automated refill system of claim 10, wherein the predictive analysis is conducted by an artificial intelligence (AI) engine, operating as the communication control logic, the first translation engine and the second translation engine.

20. The automated refill system of claim 9, wherein the second translation engine operates as a keystroke emulation logic to generate a keystroke tone corresponding to a keystoke representing the second digital data.

* * * * *